United States Patent [19]

Simpson

[11] 4,410,086

[45] Oct. 18, 1983

[54] MEDICAL APPLIANCE DISPOSAL CONTAINER

[76] Inventor: James L. Simpson, 307 MacLaren La., Lake Bluff, Ill. 60044

[21] Appl. No.: 354,951

[22] Filed: Mar. 5, 1982

[51] Int. Cl.³ .................. B65D 25/00; B26F 3/00; B65F 7/00; B65F 1/02
[52] U.S. Cl. .................. 206/366; 206/63.5; 206/380; 206/216; 206/459; 225/93
[58] Field of Search .............. 206/370, 380, 365, 366, 206/63.5, 216, 459; 225/93

[56] References Cited

U.S. PATENT DOCUMENTS

| 619,188 | 2/1899 | Kirkwood | 206/63.5 |
|---|---|---|---|
| 2,034,006 | 3/1933 | Smith | 206/63.5 |
| 3,226,007 | 12/1965 | Thies et al. | 206/365 |
| 3,796,359 | 3/1974 | Dick | 206/365 |
| 3,893,608 | 7/1975 | Koenig | 206/366 |
| 4,375,849 | 3/1983 | Hanifl | 206/63.5 |

Primary Examiner—William T. Dixson, Jr.

Attorney, Agent, or Firm—Thomas W. Speckman

[57] ABSTRACT

A medical appliance disposal container is disclosed having at least one opening for insertion of medical appliances, the opening being covered by at least one slotted plastic membrane for insertion of the desired medical appliance into the disposal container. In at least one of the openings at the end of the slot is a bending means whereby needles may be bent while attached to a syringe and the bent needle-syringe assembly inserted through the slot into the disposal container. In another embodiment, laminated plastic screens can be color-coded to aid in sorting and counting of medical appliances, such as scalpel blades, following surgery. The disposal container of this invention provides for the direct intact disposal of a wide variety of medical appliances while providing an inexpensive container for placement at a large number of locations throughout a health care facilty. The medical appliance disposal container disclosed reduces the risk of contents spillage should the container be upset during use.

25 Claims, 5 Drawing Figures

U.S. Patent  Oct. 18, 1983  4,410,086
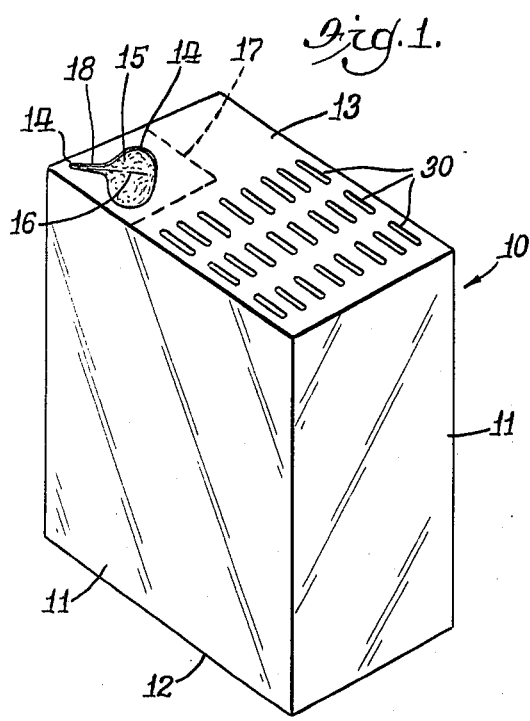
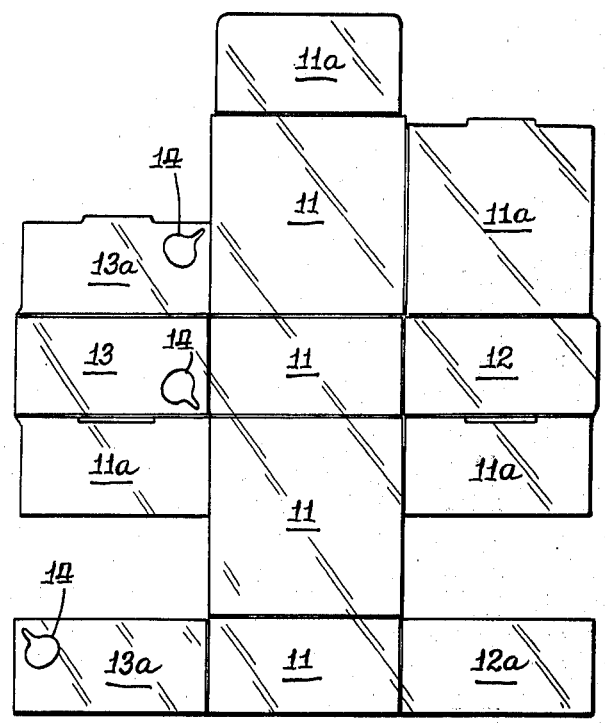
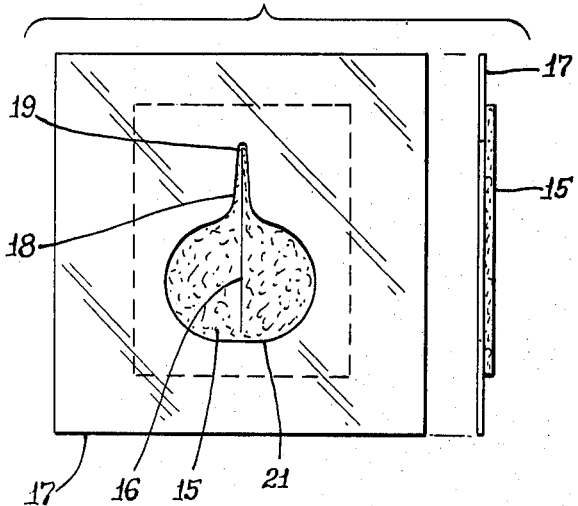
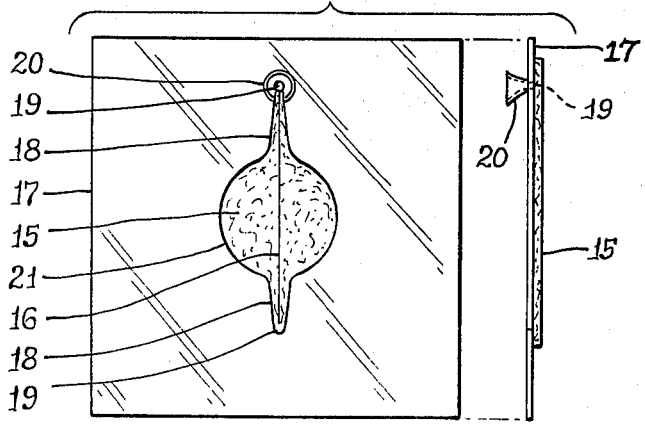
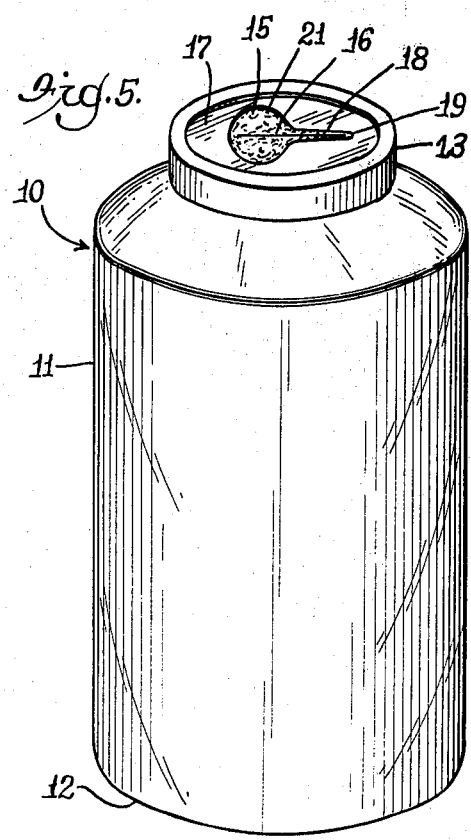

MEDICAL APPLIANCE DISPOSAL CONTAINER

BACKGROUND OF THE INVENTION

1. Field of the Invention

This invention relates to medical, dental and veterinary appliance disposal, hereinafter referred to as medical to include all fields. More particularly this invention relates to an improved apparatus for the safe disposal of potentially injurious medical appliances such as needles, syringes, scalpel blades, laboratory culture slides, blood tubing and toxic waste containers.

2. Description of the Prior Art

Potentially contagious medical waste, such as scalpel blades and particularly syringes with needles present an imminent threat of injury to patient-care personnel. Accidental needle puncture is the most frequent accident in hospitals. The Bacterial Diseases Division, Bureau of Epidemiology, Center for Disease Control, advises that disposal apparatus for such waste should be rigid containers; placed in each patient room; syringes with needles should be placed directly into the disposal container without disassembling needle from syringe; and full containers should be securely taped shut to provide safe storage prior to final disposal with other solid waste from the hospital. Contagious medical waste of the above nature presents an even more serious problem of disposal and specialized handling. Prior disposal containers, particularly for scalpel blades and syringes and needles, have been largely unable to meet the above criteria.

Prior disposal methods for medical waste have been of several types. One type requires the user to insert the needle into a clipping device which shears the needle. However, the syringe must be placed separately into a disposal container. Since the clipping device requires two hands to operate, the user must have both hands free to dispose of a needle and syringe. Moreover, the clipping device may dull and then is likely to splatter the immediate area with blood or other syringe contents. The clipping or snapping disposal techniques air mobilize microorganisms or other contaminants. Other similar methods involve chopping the assembled needle and syringe into pieces or recapping the needle and manually breaking the assembly prior to disposal. These methods result in added exposure to health care personnel.

A second general means of disposal has used a corrugated cardboard container with a slot in the top panel through which the user inserts the appliance for disposal. This type of disposal container does not include a clipping or other means for making the syringe needle inoperable. Furthermore, since the receiving slot remains open while the container is in use, there is a chance the contents could be spilled if the disposal container was upset.

SUMMARY OF THE INVENTION

This invention provides an improved apparatus for the safe disposal of potentially injurious medical appliances such as needles, syringes and scalpel blades. The medical appliance disposal container of this invention includes a bender means for bending needles mounted in the top panel of the disposal container. In one embodiment, a bender plate has a central opening sufficiently large to receive the entire medical appliance, and a tapered slot leading to a needle bending orifice. After bending the needle, the user can directly deposit the needle-syringe assembly without withdrawing the needle from the disposal container or separating the needle from the syringe. A slotted film laminated, reticulated polyurethane foam screen and a plastic membrane cover spans the bender plate opening, guides the needle to the bending orifice, and prevents spillage should the disposal container be upset during use. The laminated screens can be color-coded to aid in the sorting and counting of medical appliances, such as scalpel blades, following surgery. The inexpensive medical appliance disposal container of this invention is not limited to contagious waste and can be easily autoclaved prior to final disposal.

It is an object of this invention to provide an improved container for the safe disposal of potentially injurious medical appliances which overcomes many of the disadvantages of prior apparatus.

It is another object of this invention to provide a means for safe disposal of medical appliances which protects staff or paramedical persons from accidental needle puncture.

It is another object of this invention to provide a disposal container for the direct intact disposal of a wide variety of medical appliances.

It is still another object of this invention to provide a single disposal container capable of rendering needles inoperable.

It is yet another object of this invention to provide an inexpensive medical appliance disposal container for placement in each patient room.

It is still a further object of this invention to provide a medical appliance disposal container that reduces the risk of contents spillage should the container be upset during use.

It is another object of this invention to provide a medical appliance disposal container which shows the number of such appliances which have been inserted therein.

These and other objects, advantages and features of this invention will become apparent from the description together with the drawings.

BRIEF DESCRIPTION OF THE DRAWINGS

FIG. 1 is a perspective view of a medical appliance disposal container of one embodiment of this invention;

FIG. 2 is a flat plan view of a collapsible dispoal container of one embodiment of this invention;

FIG. 3 is a top and side view showing one embodiment of a bender plate according to this invention;

FIG. 4 is a top and side view of another embodiment of a bender plate of this invention; and FIG. 5 is a perspective view of a medical appliance disposal container of another embodiment of this invention.

DESCRIPTION OF THE PREFERRED EMBODIMENTS

FIG. 1 shows medical appliance disposal container 10 with an enclosed body portion of side walls 11, bottom 12, and top 13. It is apparent that the container top may be of separate construction or may be part of the body construction. Top 13 has container opening 14 of sufficient size for insertion of a needle-syringe assembly therethrough into the inside of the container. In association with and of the same general size as container opening 14, is syringe disposal opening 21 in bending means plate 17. As best seen in FIG. 3, syringe disposal opening 21 is covered or spanned by at least one plastic membrane 15. Plastic membrane 15 has slot 16 of sufficient size to permit insertion of the desired medical appliance into disposal container 10. Slot 16 extends substantially to the end of bending means guide slot 18 in bending means plate 17. At the end of bending means guide slot 18 is bending means orifice 19 wherein a needle mounted on a syringe may be readily bent, prohibiting further use.

It is thus seen from FIGS. 1 and 3 that the needle of an intact needle-syringe assembly may be inserted through slot 16, moved along guide slot 18 to bending orifice 19, easily bent, moved back out of guide slot 18 and the entire needle and syringe, while still assembled, deposited into the disposal container through slot 16. In a similar fashion, a bending plate may have the configuration as shown in FIG. 4 wherein the bending means orifice 19 has a bending orifice ferrule 20 extending therefrom to provide yet easier bending of the needle and to make possible the use of thinner and less stiff material for bending plate 17.

In another embodiment of this invention, medical appliance disposal container 10 may be a molded plastic container such as shown in FIG. 5 having side walls 11, bottom 12 and separate top 13. In the embodiment as shown in FIG. 5, it is readily seen that top 13 is covered by bending means plate 17 with syringe disposal opening 21, bending means guide slot 18, and bending means orifice 19, all covered by membrane 15 having slot 16 extending the length of the guide slot to the bending orifice 19. Again, any medical appliance which will fit through slot 16 may be placed in disposal container 10 and needles of needle-syringe assemblies may be inserted into slot 16 to about half their length, moved along guide slot 18 to bending orifice 20 where the needle is readily bent, and the assembly moved back along slot 16 with the needle being below membrane 15 to the central portion of syringe disposal opening 21 where the syringe body may be inserted into disposal container 10.

FIG. 2 shows the layout of a collapsible container according to one embodiment of this invention which provides a full liner for the container. The collapsible container shown collapsed in FIG. 2 has the assembled shape of the container shown in FIG. 1 with side walls 11, bottom 12 and top 13, side wall liners 11a, bottom liner 12a and two top liners 13a. In a collapsible container of this type which may be readily and cheaply constructed of cardboard, bending means plate may be aligned with container opening 14 and sandwiched between top panel 13 and liner panel 13a, or between the liner panels, preferably with adhesive means to retain the bender plate in alignment with top hole 14.

Medical appliance disposal container 10 shown in FIG. 1, in addition to the syringe needle bending opening and syringe disposal opening previously described also has medical appliance insertion openings 30. The medical appliance insertion openings 30 may be of any suitable shape to receive particular medical appliances. The medical appliance insertion openings 30, like syringe disposal opening 21, have a slotted plastic membrane covering the opening with the slot being of sufficient size to permit insertion of the desired medical appliance into the disposal container. For different medical appliances, it is convenient to have rows of openings 30 for each type of medical appliance. Further, it is particularly desirable to have the plastic membranes covering the medical appliance insertion openings 30 color-coded so that the membrane at each opening will indicate disposal of a medical appliance through that opening providing accurate count of appliances used and disposed of as will be further discussed below.

From the above general description of the medical appliance disposal container of this invention, it is apparent that a wide variety of shapes and sizes of containers may be used to fit a wide variety of specific use situations. For example, a disposal container as shown in FIGS. 1 and 2 may be fabricated from inexpensive cardboard in appropriate sizes to accommodate use in private hospital rooms, large wards, nursing stations, and specific treatment or operating rooms, as well as emergency vehicles, ambulances, and the like. The cardboard container may be coated on its interior with an absorbent material to absorb liquids or it may be coated on its interior with an absorbent resistant material to prevent liquid of liquids. Likewise, the exterior may be coated with a plastic to prevent liquid absorption and to provide easy and effective cleaning. It is readily seen that synthetic polymeric sheet material of sufficient stiffness may be substituted for cardboard in the disposal box shown in FIG. 1. Currently available blow molded plastic containers such as bottles having the shape generally shown in FIG. 5, may also be used instances where the disposal container needs to be liquid-proof. Use of the plastic bottle-type disposal container as shown generally in FIG. 5, permits utilization of a wise number of different disposal openings by simply providing different inserts for setting beneath cap 13.

Bending means plate 17 is used in connection with container openings 14 through which it is desired to dispose of needle-syringe assemblies. As described above, the bending plate provides bending orifice 19 for bending the needle while attached to the syringe and syringe disposal opening 21 of sufficient size to permit passage of the syringe body therethrough. There are many shapes and sizes of bending plates which would be suitable for use with the disposal containers of this invention as is readily apparent to one skilled in the art upon reading this disclosure. Generally, for durability, it is desirable that the bending plate be of a metallic material, but synthetic polymeric materials may also be used, particularly glass fiber reinforced sheet materials, such as glass reinforced nylon or durable plastics such as Lexan, a polycarbonate. For thinner bending plates and for bending plates constructed of materials which are less durable, it is preferable to provide bending orifice ferrule 20, as shown in FIG. 4, of metal to provide a durable bending orifice permitting direct one-handed bending and disposal of a needle-syringe assembly. Also, as shown in FIG. 4, the bending means plate may have multiple bending orifices each with their appropriate guide slot for reception of different size or different types of needles.

Syringe disposal opening 21 is completely covered by at least one slotted plastic membrane. Plastic membrane 15 preferably has a single slot 16 which extends substantially across bending means opening 21, along bending means guide slot 18 and bending orifice 19. Plastic membrane 15 is preferably sheet reticulated synthetic polymeric foam of a type which returns to its original condition following spreading of slot 16 upon insertion of a medical appliance. Suitable such films include reticulated polyurethane foam and polyvinylchloride. Multiple layers of spaced plastic membranes may be used, such as one or each side of a bending means plate or attached to container opening 14 and different top liners 13a as shown most clearly in FIG. 2. Multiple membranes, such as two or three, assure closure of the membrane following insertion of the medical appliance therethrough and provide additional strength to the open enclosure when the disposal container may be accidentally turned upside down. The single slot 16 also aids in retention of medical appliances within the disposal container when it is turned upside down. The surface of plastic membrane 15 facing the exterior of the disposal container may be a laminated smooth polymeric film for ease of cleaning.

Medical appliance insertion openings 30, used for medical appliances other than needle-syringe assemblies, may be constructed in the same fashion as described above except that the disposal opening need not provide the bending means guide slot 17 and bending means orifice 19. A bending means plate 17 is not necessary for such insertion openings. The plastic membrane may be constructed in a similar fashion and adhered directly to the bottom of container top 13 or preferably between top 13 and top liner 13a or between two layers of top liner 13a. Medical appliance insertion openings 30, of suitable shape for particular medical appliances, may be arranged in convenient rows for each type of medical appliance and slot 16 may be covered with a thin colored layer of sheet material which must be broken for insertion of the medical appliance and thus using a different hole for each medical appliance, the number of specific medical appliances inserted into the disposal container may be readily ascertained, as is necessary in various medical practices, such as insertion of scalpels from an operating procedure. It is also apparent that the opening or openings for disposal of medical appliances may also be located in the upper portion of the sides of the disposal container.

A suitable durable adhesive coated seal may be provided on the side or top of the disposal container for fully covering the openings in the top of the container for disposal of the complete container containing the disposed medical appliances. Any suitable means may be used to cover the container openings and the medical appliance disposal container then safely disposed of in accordance with recommended procedures, depending upon its contents. Contagious medical waste may be disposed of in containers according to this invention which can be autoclaved as required prior to final disposal.

An improved medical appliance disposal container has been described which protects health service personnel from needle puncture wounds, the most prevalent hospital accident. Further, the disposal container of this invention provides direct intact disposal of a wide variety of medical appliances; renders needles inoperable; reduces risk of contents spillage; and provides an inexpensive disposal container for wide usage in the health care industry.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A medical appliance disposal container comprising; a container body comprising a bottom and side walls; and a container top enclosing said container, said container top having at least one opening therein for insertion of medical appliances, said opening being covered by at least one slotted plastic membrane, said slot being of sufficient size to permit insertion of the desired medical appliance into the disposal container, and a bending means located at one end of said slot whereby needles may be bent while attached to a syringe and the bent needle-syringe assembly inserted through said slot into said disposal container.

2. The medical appliance disposal container of claim 1 wherein said bending means comprises an orifice and an orifice ferrule extending outwardly therefrom.

3. The medical appliance disposal container of claim 1 wherein said container body and said container top comprises one piece of material which is capable of being assembled to form said container from a flat sheet.

4. The medical appliance disposal container of claim 1 wherein said container body and said container top are fabricated from cardboard.

5. The medical appliance disposal container of claim 1 wherein said container has an absorbent material on its inner surface.

6. The medical appliance disposal container of claim 1 wherein said container has a non-absorbent material on its inner surface.

7. The medical appliance disposal container of claim 1 wherein said container body and said container top has a non-absorbent exterior surface.

8. The medical appliance disposal container of claim 1 wherein said container body and said container top are fabricated from synthetic polymeric sheet material.

9. The medical appliance disposal container of claim 1 having additional openings in said top for insertion of medical appliances, said additional openings being covered by at least one slotted plastic membrane, said slot being of sufficient size to permit insertion of the desired medical appliance into the disposal container.

10. The medical appliance disposal container of claim 9 wherein said additional openings are color-coded so that the membrane at each opening will indicate disposal of a medical appliance through that opening.

11. The medical appliance disposal container of claim 10 having said slot covered by a thin colored layer of sheet material which is broken upon insertion of a medical appliance.

12. The medical appliance disposal container of claim 1 wherein said bending means is constructed of materials selected from the group consisting of metallic materials, glass fiber reinforced sheet polymeric materials, and polycarbonates.

13. The medical appliance disposal container of claim 1 wherein said plastic membrane is selected from the group consisting of reticulated polyurethane foam and polyvinylchloride.

14. The medical appliance disposal container of claim 1 wherein said opening is covered by two or three said membranes.

15. The medical appliance disposal container of claim 1 wherein said opening is covered by a seal for disposal of said container.

16. The medical appliance disposal container of claim 1 wherein said container body comprises a molded plastic container and a separate container top.

17. In a medical appliance disposal container of the type having at least one opening therein for insertion of a medical appliance, the improvement comprising; said opening being covered by at least one slotted plastic membrane, said slot being of sufficient size to permit insertion of the desired medical appliance into the disposal container, and a bending means located at one end of said slot whereby needles may be bent while attached to a syringe and the bent needle-syringe assembly inserted through said slot into said disposal container.

18. The medical appliance disposal container of claim 17 wherein said bending means comprises an orifice and an orifice ferrule extending outwardly therefrom.

19. The medical appliance disposal container of claim 17 having additional openings therein for insertion of medical appliances, said additional openings being covered by at least one slotted plastic membrane, said slot being of sufficient size to permit insertion of the desired medical appliance into the disposal container.

20. The medical appliance disposal container of claim 19 wherein said additional openings are color-coded so that the membrane at each opening will indicate disposal of a medical appliance through that opening.

21. The medical appliance disposal container of claim 20 having said slot covered by a thin colored layer of sheet material which is broken upon insertion of a medical appliance.

22. The medical appliance disposal container of claim 17 wherein said bending means is constructed of materials selected from the group consisting of metallic materials, glass fiber reinforced sheet polymeric materials, and polycarbonates.

23. The medical appliance disposal container of claim 17 wherein said plastic membrane is selected from the group consisting of retirulated polyurethane foam and polyvinylchloride.

24. The medical appliance disposal container of claim 17 wherein said opening is covered by two or three said membranes.

25. The medical appliance disposal container of claim 17 wherein said opening is covered by a seal for disposal of said container.

* * * * *